United States Patent [19]

Schreiber et al.

[11] 4,191,660
[45] Mar. 4, 1980

[54] ORGANOLEPTIC USES OF 1-(3,3-DIMETHYL-2-NORBORNYL)-2-PROPANONE IN CATIONIC, ANIONIC AND NONIONIC DETERGENTS AND SOAPS

[75] Inventors: William L. Schreiber, Jackson; James N. Siano, Keyport; Manfred H. Vock, Locust, all of N.J.; Edward J. Shuster, Brooklyn, N.Y.

[73] Assignee: International Flavors & Fragrances Inc., New York, N.Y.

[21] Appl. No.: 932,615

[22] Filed: Aug. 10, 1978

Related U.S. Application Data

[60] Continuation-in-part of Ser. No. 881,331, Feb. 27, 1978, abandoned, which is a division of Ser. No. 819,951, Jul. 28, 1977, Pat. No. 4,090,985, which is a division of Ser. No. 747,308, Dec. 3, 1976, Pat. No. 4,053,657.

[51] Int. Cl.$^2$ .......................... C11D 9/44; C11D 3/50
[52] U.S. Cl. ........................ 252/174.11; 252/522 R; 260/586 G
[58] Field of Search .............. 252/89, 522; 260/586 G

[56] References Cited
U.S. PATENT DOCUMENTS 4,076,853  2/1978  Light et al. ..................... 252/89 R Primary Examiner—Mayer Weinblatt
Attorney, Agent, or Firm—Arthur L. Liberman; Franklin D. Wolffe

[57] ABSTRACT

Processes and compositions are described for the use in cationic, anionic and nonionic detergents and soaps of 1-(3,3-dimethyl-2-norbornyl)-2-propanone (hereinafter referred to as the "norbornylpropanone derivatives") having the structure:

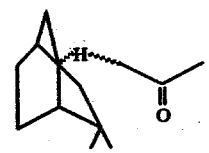

(which structure is intended to cover both the "endo" and the "exo" isomers thereof). Addition of the said "norbornylpropanone derivative" to soaps and cationic, anionic and nonionic detergents is indicated to produce sweet, berry, woody, piney, mint aroma notes with a damascenone-like character and buttery and minty nuances.

2 Claims, 2 Drawing Figures

I R SPECTRUM FOR EXAMPLE I

ORGANOLEPTIC USES OF 1-(3,3-DIMETHYL-2-NORBORNYL)-2-PROPANONE IN CATIONIC, ANIONIC AND NONIONIC DETERGENTS AND SOAPS

This application is a continuation-in-part of application for U.S. Letters Patent Ser. No. 881,331 filed on Feb. 27, 1978 now abandoned, which, in turn, is a divisional of application for U.S. Letters Patent Ser. No. 819,951 filed on July 28, 1977 (now U.S. Pat. No. 4,090,985 issued on May 23, 1978), which is in turn a divisional of application for U.S. Letters Patent Ser. No. 747,308, filed on Dec. 3, 1976, now U.S. Pat. No. 4,053,657 issued on Oct. 11, 1977.

BACKGROUND OF THE INVENTION

The present invention relates to 1-(3,3-dimethyl-2-norbornyl)-2-propone and compsitions using said "norbornylpropane derivative" to augment or enhance the flavor and/or aroma of consumable materials or impart flavor and/or aroma to consumable materials.

There has been considerable work performed relating to substances which can be used to impart (modify, augment or enhance) flavors and fragrances to (or in) various consumable materials. These substances are used to diminish the use of natural materials, some of which may be in short supply and to provide more uniform properties in the finished product.

Fruity/berry, pine needle-like aromas with sweet, fruity/berry, blueberry-like, pine needle-like and pine balsam flavor characteristics are particularly desirable for many uses in foodstuffs flavors, chewing gum flavors, toothpaste flavors and medicinal product flavors.

Sweet, berry, woody, piney, mint aroma notes with a damascenone-like character and buttery and minty nuances are desirable in several types of perfume compositions, perfumed articles and colognes.

U.S. Pat. No. 3,852,358 issued on Dec. 3, 1974 discloses a process for producing 2-acetyl-3,3-dimethyl-5-norbornene in both the exo and endo forms which have uses in perfumery and other fragrance applications. These compounds have the structures:

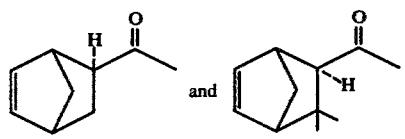

These compounds, produced by reaction of cyclopentadiene with mesityl oxide, are starting materials for producing a number of the compounds of our invention. However, the compounds of our invention have unexpected, unobvious and advantageous properties when compared with the 2-acetyl-3,3-dimethyl-5-norbornene of U.S. Pat. 3,852,358.

U.S. Pat. No. 3,942,761 discloses the use in perfumery of 4(2'-norbornyl)-2-butanones having the structure:

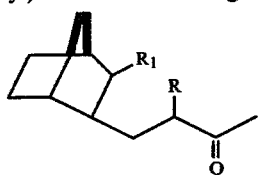

wherein $R_1$ is hydrogen or methyl and R is hydrogen or lower alkyl containing from 1 to 8 carbon atoms. Such compounds have structures which are different in kind from the structures of the compounds of our invention. Also disclosed as intermediates for producing the foregoing compounds are compounds having the generic structure:

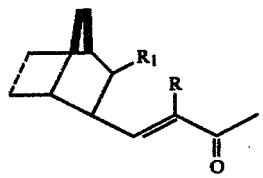

wherein the dotted line is a carbon-carbon single bond or a carbon-carbon double bond. In addition, the following reaction sequence is set forth therein:

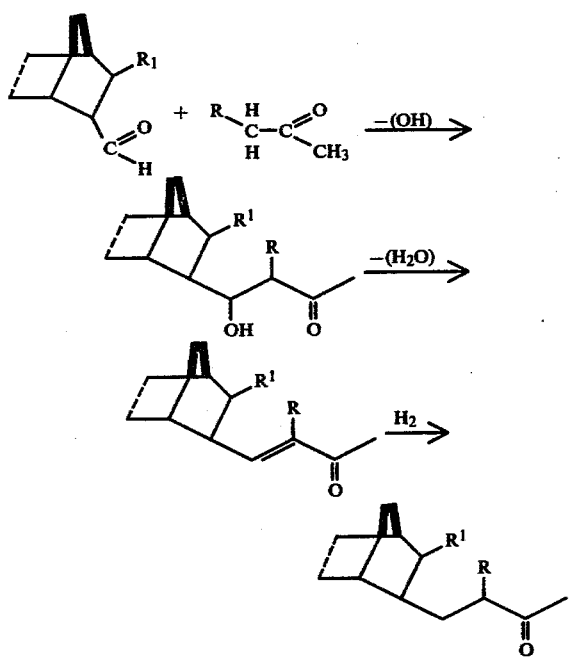

Arctander, "Perfume and Flavor Chemicals," 1969, Vol. 1, discloses the use in perfume compositions and in foodstuff flavors of "fenchone," "fenchyl alcohol," "camphene carbinol," and "camphene carbinyl acetate," thus:

(i) "1385: FENCHONE
laevo-Fenchone. (dextro- is known but less common as a fragrance material).
1,3,3-Trimethyl-2-norbornanone.
1,3,3-Trimethyl bicyclo-1,2,2-heptanone-2.

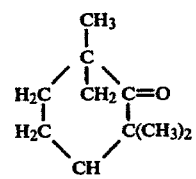

Warm-camphoraceous, powerful and diffusive, basically sweet odor.

Warm, somewhat burning and bitter taste with a medicinal note.

This ketone finds some use as a masking odor in industrial fragrances. It is also used in the reconstruction of Fennel oil and a few other essential oils.

In spite of its rather unpleasant taste, it is used in various Berry complex flavors, in Spice complexes and in certain types of Liquer flavoring.

The concentration used is about 0.1 to 5ppm in the finished product."

(ii) "1387: FENCHYL ALCOHOL
1,3,3-Trimethyl-2-norbornanol.
1,3,3-Trimethyl bicyclo-1,2,2-heptanol-2.
2-Fenchanol.
Fenchol.

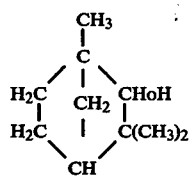

Powerful and diffusive, Camphor-like, but sweeter and more Citrus-like almost Lime-like odor with more or less of an earthy-dry character, according to the composition and isomer-ratio.

The taste is somewhat bitter-Lime-like, camphoraceous and slightly woody-musty.

This interesting alcohol (or mixed alcohols) finds use in perfume compositions ranging from woody or herbaceous to Citrus-Lime and even certain floral types. It produces power and "lift" to floral fragrances, and solid background to Lime and other Citrus bases, having the advantage over the Terpenes in being very stable in soap.

Fenchyl alcohol is also used in flavor compositions such as Strawberry and other berries, Lime and Spice, etc.

The concentration is normally low, e.g. 0.2 up to 5 ppm in the finished product".

(iii) "1028: 3,3-DIMETHYL-$\Delta^2$, beta-NORBORNANE-2-ETHANOL "Camphene carbinol."

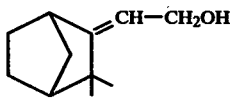

Sweet-camphoraceous, warm and soft odor with a woody undertone. Upon standing it may develop an odor resembling that of Celluloid.

Although rarely offered commercially, this chemical could find some use in perfume compositions of the woody, Oriental and orrisy type, in new variations of Pine fragrances, and in various soap and detergent perfumes."

(iv) "1029: 3,3-DIMETHYL-$\Delta^2$-beta-NORBORNANE-2-ETHYLACETATE
"Camphene carbinyl acetate."

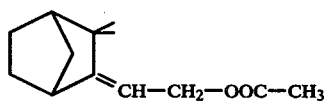

Mild and sweet-woody odor with a floral-piney undertone. The commercial products are probably not well-defined single chemicals, and great variations in odor have been observed.

This ester has been developed in line with the research on Sandalwood type odors. The parent alcohol "Camphene carbinol" was once considered useful as a Sandalwood type material, but it has found more use as a sweetening and enriching ingredient in sophisticated Pine fragrances. The title ester finds limited use in perfume compositions of woody character, Fougeres, Pine of ragrances, etc. and it blends very well with the Cyclohexanol derivatives, Ionones, iso-Bornylacetate, Nitromuska, etc."

U.S. Pat. No. 3,928,456 discloses monocyclic compounds having the generic structure:

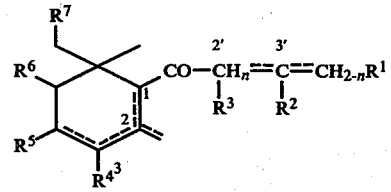

containing one double bond in position 2'-or 3'-of the acyl side-chain and either one double bond in position 1-or 2-(as shown in the above formula, the double bond in the 2 position can be either in the cycle or the side chain), or two conjugated double bonds in positions 1- and 3- of the cycle, the double bonds being represented by dotted lines, and wherein n is zero or 1, $R^1$, $R^2$ and $R^3$ represent hydrogen or one of them a lower alkyl radical, such as methyl or ethyl, and the others hydrogen, and $R^4$, $R^5$, $R^6$ and $R^7$ represent hydrogen or one of them a lower alkyl radical, such as methyl or ethyl, and the others hydrogen, as being useful in perfumery and food flavors and also flavors, beverages, animal feeds and tobaccos. Specifically disclosed in this patent is a compound having the structure:

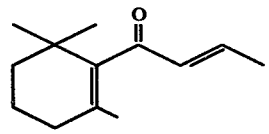

U.S. application for Letters Patent Ser. No. 551,030, filed on Feb. 19, 1975 discloses, interalia, perfumery uses of compounds having the structures:

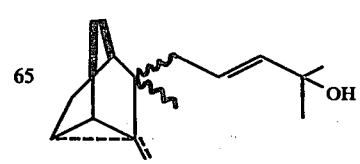

-continued

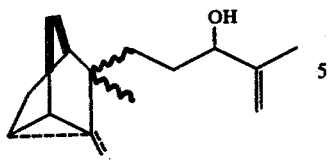

wherein one of the dashed lines is a carbon-carbon bond and each of the wavy lines is a carbon-carbon single bond, one of the carbon-carbon single bonds represented by the wavy line being epimeric with respect to the other of the carbon-carbon single bonds represented by the wavy line.

In addition, various processes and compounds relating to the synthetsis of synthetic sandalwood oil components are described in the following U.S. patents:

(i) Perfume Compounds And Process For Preparing Same U.S. Pat. No. 3,673,261 issued June 27, 1972:
   Compounds:

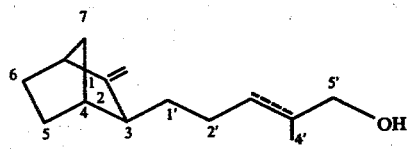

2-methylene-3-exo(trans-4'-methyl-5'-hydroxypent-3'-enyl)bicyclo[2.2.1]-heptane    trans-3-Normethyl-beta-santalol

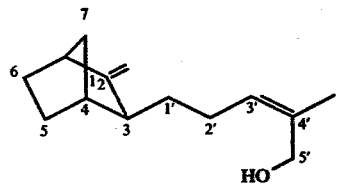

2-methylene-3-exo(cis-4'-methyl-5'-hydroxypent-3'-enyl)bicyclo[2.2.1]-heptane    cis-3-normethyl-beta-santalol

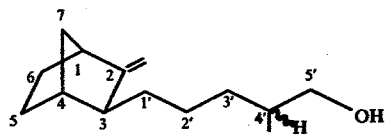

2-methylene-3-exo(4'-methyl-5'-hydroxypentyl)bicyclo[2.2.1]heptane-3-normethyldihydro-beta-santalol (ii) Dihydro-beta-santalol and Processes For Preparing Dihydro-beta-Santalol From 3-Endo-Methyl-3-Exo(4'-Methyl-5'-Hydroxyphenyl) Norcamphor — U.S. Pat. No. 3,673,263 issued June 27, 1972:

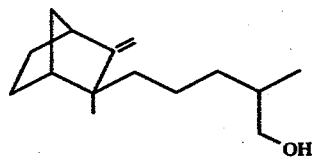

(iii) Process for Preparing Beta-Santalol From 3-Methylnorcamphor — U.S. Pat. No. 3,662,008 issued May 9, 1972:

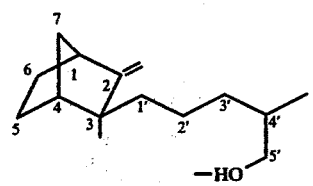

endo-3-methyl-exo-3(cis-5'- hydroxy-4'-methylpent-3'-enyl)-2-methylenebicyclo-(2.2.1) heptane

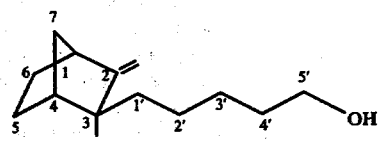

endo-3-methyl-exo-3(trans-5'-hydroxy-4'-methylpent-3'-enyl)-2-methylenebicyclo(2.2.1) heptane (iv) Process for Preparing Dihydro-Beta-Santalol From 3-Endo-Methyl-3-Exo(4'-Methyl-5'-Hydroxypentyl) Norcamphor — U.S. Pat. No. 3,673,266, issued June 27, 1972:

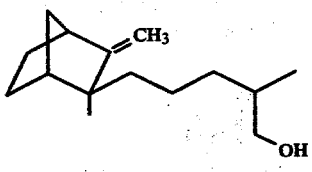

dihydro-beta-santalol

None of the compounds disclosed in either U.S. Pat. No. 3,928,456 or U.S. application for Letters Patent Ser. No. 551,030, filed Feb. 19, 1975 have properties even closely similar to the properties of the "norbornylpropanone derivative" of the instant application.

Chem. Abstracts, Vol. 84, 73728n (abstract of Karaev, et al, Zh.Org.Khim. 1975, 11(12), 2622) discloses preparation of the compound:

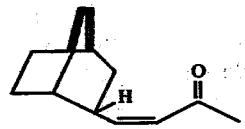

Klein and Rojahn, Chem.Abstracts, Vol. 84, 90327y (1976) discloses the use of compounds having the generic structure:

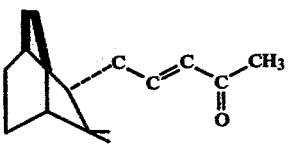

(wherein the dashed line is a single or double bond) as an intermediate in the preparation of beta-santalol; but no organoleptic properties of these norbornane derivatives are disclosed.

U.S. Pat. No. 3,748,344, issued on July 24, 1973, discloses that chemical compounds characterized by the structural formula:

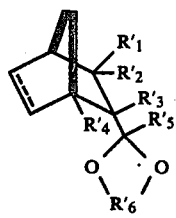

wherein the dashed line represents the presence of a single or a double bond wherein $R_1'$, $R_2'$, $R_3'$, and $R_4'$ each represent hydrogen or lower methyl and $R_5'$ represents hydrogen or lower alkyl and $R_6'$ represents a polymethylene radical of from 2 to 4 carbon atoms which is unsubstituted or substituted with lower alkyl, which "as a whole exhibits a characteristic, pleasant, strong and long lasting aroma which is highly useful in the preparation of fragrance compositions and perfume products." Various notes are described such as green, cuminic, walnut raw potatoe, earthy, camphoraceous, civet, walnut bark, neroli, anise, vegetable, menthone, animal, minty, eucalyptol, cucumber, pine and fecal.

In addition, U.S. Pat. No. 3,748,344 discloses as chemical intermediates for preparing the above ketal, a compound having the generic structure:

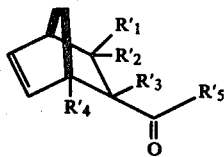

wherein $R_1'$, $R_2'$, $R_3'$, $R_4'$ and $R_5'$ have the same meaning as defined above.

However, the specific compound of our invention is not set forth in U.S. Pat. No. 3,748,344.

No prediction of the organoleptic properties of the compound of the instant invention can be made by a study of the disclosure of U.S. Pat. No. 3,748,344.

Chemical Abstracts, Vol. 71, 496634z (abstract of Sadykh-Zade, et al (U.S.S.R.) Dokl. Akad. Nauk Azerb. SSR 1968, 24(11), 38–41) discloses the synthesis of exo and endo forms of the compounds having the structures:

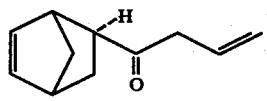

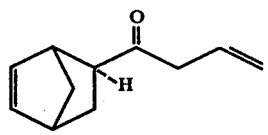

Chemical Abstracts, Vol. 81, 135512m (abstract of Akhmedov, I.M., et al (Inst. Georg. Fiz. Khim., Baku, U.S.S.R.). Dokl. Akad. Nauk Az. SSR 1974, 30(4), 18–21) discloses the synthesis of the compound having the structure:

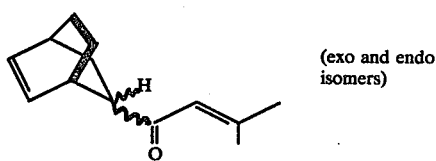

(exo and endo isomers)

None of the Chemical Abstracts references discloses compounds which have a close structural relationship to the compound of the instant invention. In any event, the organoleptic properties of the compounds of the Chemical Abstract references are different in kind from those of the compound of the instant invention.

THE INVENTION

Figure 1:
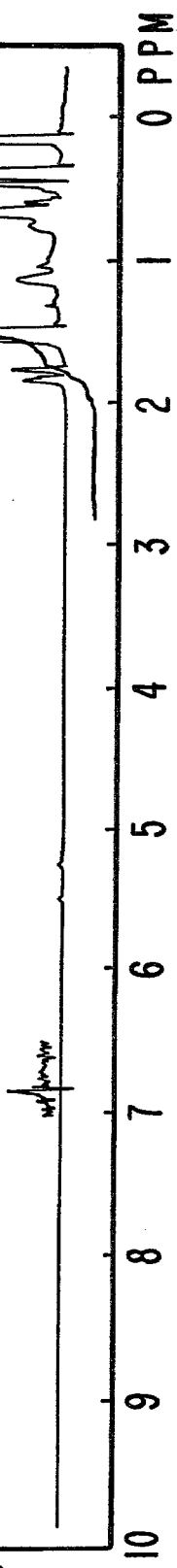
FIG. 1 is the NMR spectrum for the "norbornylpropanone derivative" of our invention produced in Example I.

It has now been discovered that novel solid and liquid foodstuff, chewing gum, medicinal product and toothpaste compositions and flavoring compositions therefor having fruity/berry, pine needle-like aromas and sweet, fruity/berry, blueberry-like, pine needle-like, pine balsam flavor characteristics and novel perfume compositions, colognes and perfumed articles having sweet, berry, woody, piney, mint aroma notes with a damascenone-like character and buttery and minty nuances, may be provided by the utilization of the compound 1-(3,3-dimethyl-2-norbornyl)-2-propane having the structure:

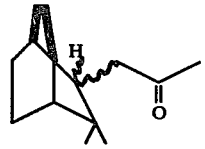

as the "endo" form or the "exo" form of the "exo" form or a mixture of "endo" and "exo" forms.

The 1-(3,3-dimethyl-2-norbornyl)-2-propanone useful as indicated supra may be produced according to a process of reacting acetaldehyde with camphene in the presence of a free radical initiator, as in the process set forth by Suga and Watanabe, Aust. Jour. of Chemistry, 20(9), 2033–6 (1967) and Kheifits, et al, Zh. Org. Khim., 1969, 5(9) 1636–9. It can also be produced by ultraviolet irradiation of acetaldehyde and camphene in the presence of an efficient hydrogen abstractor such as a 1,2-diketone as set forth in Example I.

When the "norbornylpropane derivative" of our invention is used as a food flavor adjuvant, the nature of the coingredients included with said "norbornylpropanone derivative" in formulating the product composition will also serve to alter, modify, augment or enhance the organoleptic characteristics of the ultimate foodstuff treated therewith.

As used herein in regard to flavors, the terms "alter", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the "norbornylpropanone derivative" of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature.

It is a requirement that any such material be "ingestibly" acceptable and thus non-toxic and otherwise non-deleterious particulary from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, petines, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanol, crotonal, diacetyl, 2-methyl butanal, beta, beta-dimethylacrolein, methyl-n-amyl ketone, n-hexanol, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentonal, furfural, 5-methyl furfural, cinnamaldehyde, beta-cyclomocitral, 2-pentanone, 2-pentenal and propanal; alcohols such as 1-butanol, benzyl alcohol, 1-borneol, trans-2-buten-1ol, ethanol, geraniol, 1-hexanal, 2-heptanol, trans-2-hexenol-1, cis-3-hexen-1-ol, 3-methyl-3-buten-1ol, 1-pentanol, 1-penten-3-ol p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl napthalene, dodexane, methyl diphenyl, methyl naphthalene, myrcene, naphthalene, octadecane, tetradecane, tetramethyl naphthalene, tridecane, trimethyl naphthalene, undecane, caryophyllene, 1-phellandrene, p-cymene, 1-alpha-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone; sulfides, e.g., methyl sulfide and other materials such as maltol, acetoin and acetals (e.g., 1,1-diethoxy-ethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the "norbornylpropanone derivative" of our invention by not covering or spoiling the organoleptic properties (aroma and/or taste) thereof; (ii) be nonreactive with the "norbornylpropanone derivative" of our invention and (iii) be capable of providing an environment in which the "norbornylpropanone derivative" can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid product, e.g., simulated foodstuffs, ingredients capable of providing normally solid compositions should be selected such as various cellulose derivatives.

As will be appreciaed by those skilled in the art, the amount of "norbornylpropanone derivative" employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of "norbornylpropanone derivative" will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of "norbornylpropanone derivative" ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the "norbornylpropanone derivative" is added to the foodstuff as an integral component of a flavoring composition, it is, of course, essential that the total quantity of flavoring composition employed be sufficient to yield an effective "norbornylpropanone derivative" concentration in the foodstuff product.

Food flavoring compositions prepared in accordance with the present invention preferably contain the "norbornylpropanone derivative" in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the "norbornylpropanone derivative" with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the "norbornylpropanone derivative" in a dry blender until the requisite degree of uniformity is achieved.

It is presently preferred to combine with the "norbornylpropanone derivative" of our invention, the following adjuvants:
p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl perlargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl-ether;
Diacetyl;
Furfural;
Ethyl acetate;
Anethole;
2,3-Dimethyl pyrazine;
2-Ethyl-3-methyl pyrazine;

3-Phenyl-4-pentenal
2-Phenyl-2-hexenal;
2-Phenyl-2-pentenal;
3-Phenyl-4-pentenal diethyl acetal;
Beta-damascone (1-crotonyl-2,2,6-trimethylcyclohex-1-one)
Damascenone (1-crotonyl-2,2,6-trimethylcyclohexa-1,5-diene);
Beta-cyclohomocitral (2,2,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxy benzene;
Isoelemecine (4-propenyl-1,2,6-trimethoxy benzene; and
2-(4-Hydroxy-4-methylpenyl) norbornadiene prepared according to U.S. Application for Letters Patent 461,703, filed on April 17, 1974

The "norbornylpropanone derivative" and one or more auxiliary perfume ingredients, including, for example, alcohols, aldehydes, nitriles, esters, cyclic esters and natural essential oils, may be admixed so that the combined odors of the individual components produce a pleasant and desired fragrance, particularly and preferably in woody and/or piney fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however, the over-all sensory effect of the perfume composition will be at least the sum total of the effects of each of the ingredients. Thus, the "norbornylpropanone derivative" of our invention can be used to alter, modify or enhance the aroma characteristics of a perfume composition, for example, by utilizing or moderating the olfactory reaction contributed by another ingredient in the composition.

The amount of "norbornylpropanone derivative" of our invention which will be effective in perfume compositions as well as in perfumed articles and colognes depends on many factors, including the other ingredients, their amounts and the effects which are desired. It has been found that perfume compositions containing as little as 0.01% of "norbornylpropanone derivative" or even less (e.g., 0.005%) can be used to impart a sweet, berry, woody, piney, minty aroma with damascenone-like nuances to soaps, cosmetics or other products. The amount employed can range up to 70% of the fragrance components and will depend on considerations of cost, nature of the end product, the effect desired on the finished product and the particular fragrance sought.

The "norbornylpropanone derivative" of our invention is useful [taken alone or together with other ingredients in perfume compositions] as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and such screens; powders, such as talcs, dusting powders, face powders and the like. When used as (an) olfactory component(s) as little as 1% of the "norbornylpropanone derivative" of our invention will suffice to impart an intense sweet, berry, woody, piney, minty aroma with damascenone-like nuances to woody and/or piney and/or herbal formulations. Generally, no more than 3% of the "norbornylpropanone derivative" of our invention, based on the ultimate end product, is required in the perfume composition.

In addition, the perfume composition or fragrance composition of our invention can contain a vehicle, or carrier for the "norbornylpropanone derivative." The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the "norbornylpropanone derivative" of our invention can be utilized to alter, modify or enhance sensory properties, particularly organoleptic properties, such as flavor(s) and/or fragrance(s) of a wide variety of consumable materials.

The following Examples serve to illustrate our invention and this invention is to be considered restricted thereto only as indicated in the appended claims.

All parts and percentages given herein are by weight unless otherwise specified.

EXAMPLE I

Preparation of 1-(3,3-Dimethyl-2-Norbornyl)-2-Propanone

A 1 liter water jacketed photochemical reaction vessel equipped with magnetic stirrer and pyrex immersion well is charged with 418 g camphene (80%, Aldrich) and 372 g acetaldehyde and 30 g diacetyl (photochemical hydrogen abstractor). The mixture is irradiated with a 450 medium pressure mercury lamp (Hanovia) for 55 hours, during which time five 30 g portions of diacetyl are added at varying intervals. The reaction mixture is combined with 150 g of 1,2,4-trimethyl benzene and washed with water. The material is distilled without fractionation and then redistilled through a 5' Vigreux column to yield 224 g colorless product, b.p. 70°–72° (55 mm Hg).

The NMR spectrum is as follows:

| $\delta$, ppm | Assignment |
|---|---|
| 0.74 (s, 3H) | gem dimethyl protons |
| 0.99 (s, 3H) | |
| 1.15–2.0 (m, 7H) | $-CH_2-$ and $-\overset{\mid}{\underset{\mid}{C}}H$ |
| 2.08 (s, 3H) | $-\overset{O}{\underset{\parallel}{C}}-CH_3$ |
| 2.40 (d, J = 7Hz, 2H) | $-CH_2-\overset{O}{\underset{\parallel}{C}}-$ |

The infrared data is as follows: 2960, 1717, 2885 cm$^{-1}$

The Mass Spectral data is as follows: m/e 43, 111, 41, 122, 39, 67

Figure 2:
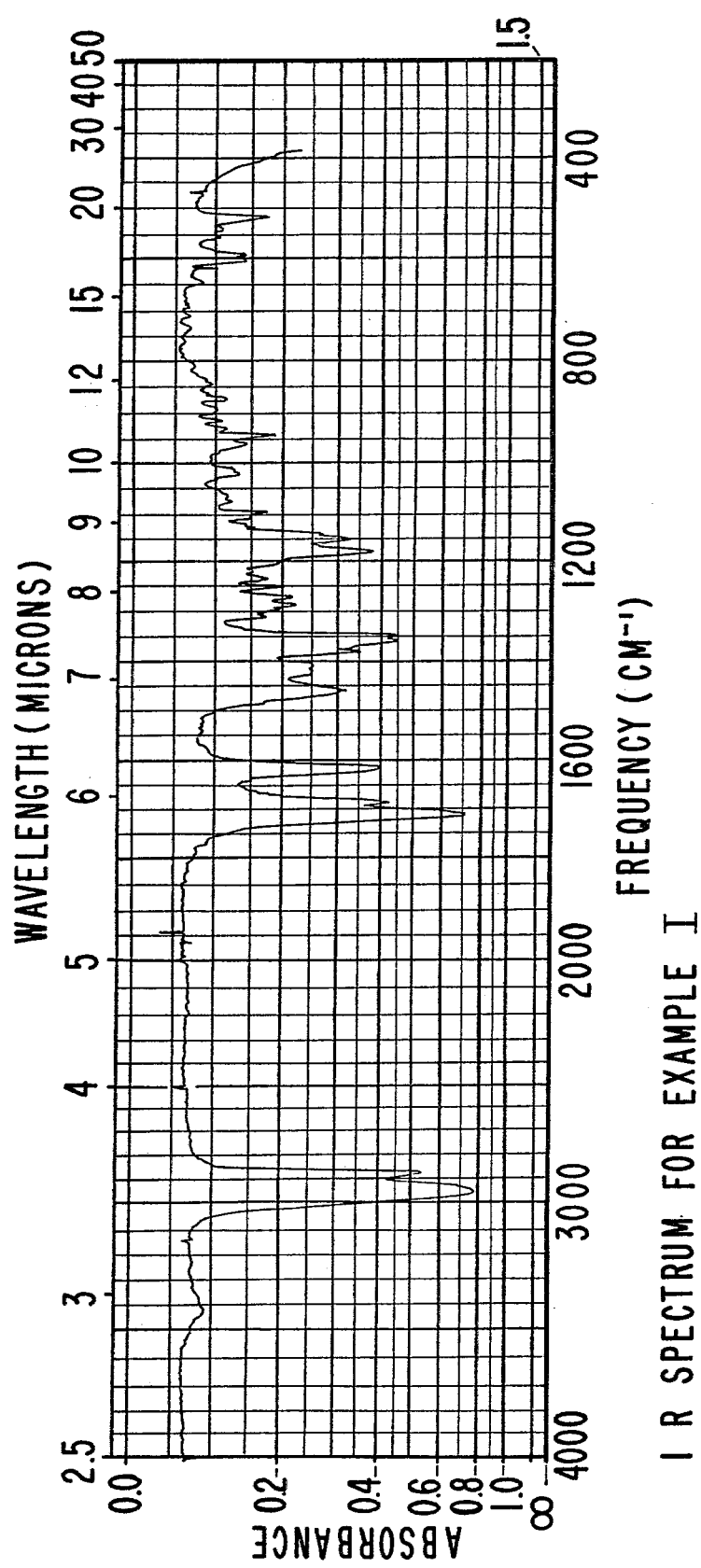
FIG. 2 is the Infrared spectrum for the "norbornylpropanone derivative" of our invention produced in Example I.

The NMR spectrum is set forth in FIG. 1. The Infrared spectrum is set forth in FIG. 2.

EXAMPLE II

FLAVOR FORMULATION USING THE MATERIAL PRODUCED IN EXAMPLE I

The following mixture is prepared:

| Ingredient | Parts by Weight |
|---|---|
| Para-hydroxy benzyl acetone | 5 |
| Vanillin | 2 |
| Maltol | 3 |
| alpha-Ionone (1% solution in propylene glycol) | 15 |
| Isobutyl Acetate | 15 |
| Ethyl Butyrate | 5 |
| Ethyl Acetate | 5 |
| Dimethyl Sulfide (10% solution in propylene glycol) | 5 |
| Acetic acid | 15 |
| Acetaldehyde | 20 |
| Propylene Glycol | 910 |
| 1-(3,3-dimethyl-2-norbornyl)-2-propanone produced in Example I | 3 |

When 1-(3,3-dimethyl-2-norbornyl)-2-propanone is added to the above formulation it adds an excellent raspberry kernel character causing the formulation to be much more natural in taste and aroma. The formulation is preferred over the same formulation not containing the 1-(3,3-dimethyl-2-norbornyl)-2-propanone.

EXAMPLE III

A perfume composition is prepared by admixing the following ingredients in the indicated proportions:

| Ingredient | Amount (Grams) |
|---|---|
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| 1-(3,3-dimethyl-2-norbornyl)-2-propanone produced according to Example I | 10 |
| Cyclized Bicyclo C-12 material produced according to the process of Example IV of Canadian Patent 854,225, issued on October 20, 1970 | 5 |
| Isobornyl cyclohexyl alcohol | 10 |
| Benzyl Acetate | 25 |
| 2-n-Heptyl cyclopentanone | 5 |
| | 353.3 (TOTAL) |

The foregoing blend is evaluated and found to have a high degree of richness and persistence in its novel natural piney quality. This base composition can be admixed with aqueous ethanol, chilled and filtered to produce a finished cologne. The cologne so prepared has a sweet, berry, woody, piney, mint aroma note with a damascenone-like character and buttery and minty nuances, The base composition can also be used to scent soap or other toilet goods such as lotions, aerosols, sprays and the like.

EXAMPLE IV

Preparation of a Cosmetic-Power Composition

A cosmetic power is prepared by mixing in a ball mill, 100 g of talcum powder with 0.25 g of 1-(3,3-dimethyl-2-propanone prepared according to Example I. It has an excellent sweet, berry, woody, piney, mint aroma with a damascenone-like character and buttery and minty nuances.

EXAMPLE V

Preparation of a Detergent Composition

A total of 100 grams of a detergent powder (a nonionic detergent powder containing a proteolytic enzyme prepared according to Example 1 of Canadian Pat. No. 985,190 issued on March 9, 1976) is mixed with 0.15 grams of 1-(3,3-dimethyl-2-norbornyl)-2-propanone prepared according to Example I until a substantially homogeneous composition is obtained. This composition has an excellent sweet, berry, woody, piney, mint aroma with a damascenone-like character and buttery and minty nuances.

EXAMPLE VI

Perfumed Liquid Detergents

Concentrated liquid detergents with rich, pleasant, sweet, berry, woody, piney and mint aromas with damascenone-like character and buttery and minty nuances are prepared containing 0.10%, 0.15% and 0.20% of 1-(3,3-dimethyl-2-norbornyl)-2-propanone prepared according to Example I. They are prepared by adding and homogeneously admixing the appropriate quantity of 1-(3,3-dimethyl-2-norbornyl)-2-propanone in the liquid detergent. The liquid detergents are all produced using anionic detergents containing a 50:50 mixture of sodium lauroyl sarcosinate and potassium N-methyl lauroyl taruide. The detergents all possess excellent sweet, berry, woody, piney mint aromas with damascenone-like character and buttery and minty nuances, the intensity increasing with greater concentration of 1-(3,3-dimethyl-2-norbornyl)-2-propanone prepared according to Example I.

EXAMPLE VII

Variegated soap bars are prepared according to Example I at column 10 of U.S. Pat. No. 4,077,754 whereby a soap mass in the form of white chunks having the following composition by weight is fed into a preplodder as described in said U.S. Pat. No. 4,077,754:

| SOAP MASS COMPOSITION | |
|---|---|
| Tallow and Coconut Sodium Soaps at 50% each by weight | 78.5% |
| Coconut Fatty Acid | 7.0% |
| Water | 11.0% |
| NaCl | 1.1% |
| Sanitizer | .5% |
| Perfume Composition prepared according to Example III | 1.6% |
| Misc. and TiO$_2$ Whitener | Balance to 100.00% |

The resulting striped soap prepared according to said Example I of U.S. Pat. No. 4,077,754 has an excellent sweet, berry, woody, piney, mint aroma note with damascenone-like character and buttery and minty nuances.

What is claimed is:

1. A process for augmenting or enhancing the aroma of a solid or liquid detergent consisting essentially of the step of intimately admixing with a solid or liquid detergent base a compound having the structure:

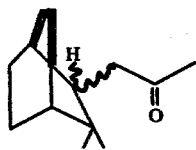
wherein the wavy lines are representative of "exo" or "endo" configurations.
2. The process of claim 1 wherein the solid or liquid detergent is a soap base.
* * * * *